United States Patent
Galavotti et al.

(10) Patent No.: US 10,617,804 B2
(45) Date of Patent: Apr. 14, 2020

(54) INTEGRATED AUTOTRANSFUSION BOWL AND FLUID LINE ORGANIZER

(71) Applicant: Sorin Group Italia S.r.l., Milan (IT)

(72) Inventors: Andrea Galavotti, Mirandola (IT); Elisa Maculan, San Felice sul Panaro (IT); Giampaolo Simonini, Reggio nell'Emilia (IT); Ivo Panzani, Mirandola (IT)

(73) Assignee: Sorin Group Italia S.r.l., Milan (IT)

( * ) Notice: Subject to any disclaimer, the term of this patent is extended or adjusted under 35 U.S.C. 154(b) by 348 days.

(21) Appl. No.: 15/521,040

(22) PCT Filed: Oct. 23, 2014

(86) PCT No.: PCT/IB2014/065558
§ 371 (c)(1),
(2) Date: Apr. 21, 2017

(87) PCT Pub. No.: WO2016/063111
PCT Pub. Date: Apr. 28, 2016

(65) Prior Publication Data
US 2017/0340785 A1    Nov. 30, 2017

(51) Int. Cl.
*A61M 1/02* (2006.01)
*B04B 5/04* (2006.01)
(Continued)

(52) U.S. Cl.
CPC ........ *A61M 1/0281* (2013.01); *A61M 1/3692* (2014.02); *A61M 1/3696* (2014.02);
(Continued)

(58) Field of Classification Search
CPC .............. A61M 1/0281; A61M 1/3696; A61M 1/3692; B04B 5/0442; B04B 7/00; B04B 7/08
See application file for complete search history.

(56) References Cited

U.S. PATENT DOCUMENTS

| 4,142,670 A | 3/1979 | Ishimaru et al. |
| 5,387,174 A * | 2/1995 | Rochat ................. B04B 5/0442 494/10 |

(Continued)

FOREIGN PATENT DOCUMENTS

| EP | 1709983 A2 | 10/2006 |
| JP | 5145497 A | 4/1976 |

(Continued)

OTHER PUBLICATIONS

Office Action issued in Japanese Application No. 2017-522099 dated Nov. 19, 2018 (with English translation), 6 pages.
(Continued)

*Primary Examiner* — Leslie R Deak
(74) *Attorney, Agent, or Firm* — Faegre Drinker Biddle & Reath LLP

(57) ABSTRACT

An autotransfusion system for separating fluid constituents includes a centrifuge housing and a rotatable driving member mounted within the centrifuge housing. The rotatable driving member is configured to receive therein and rotationally engage any one of a plurality of centrifuge bowls with different heights. In some embodiments, the centrifuge bowl is integrated with a fluid line organizer to provide for easy and efficient organization of a plurality of different fluid lines incorporated into the autotransfusion system. In some embodiments, the centrifuge bowl and fluid line organizer are easily and efficiently coupled to the centrifuge housing for autotransfusion processing.

20 Claims, 10 Drawing Sheets

(51) Int. Cl.
*B04B 7/00* (2006.01)
*B04B 7/08* (2006.01)
*A61M 1/36* (2006.01)

(52) U.S. Cl.
CPC .............. *B04B 5/0442* (2013.01); *B04B 7/00* (2013.01); *B04B 7/08* (2013.01); *A61M 2205/12* (2013.01)

(56) References Cited

U.S. PATENT DOCUMENTS

| | | |
|---|---|---|
| 6,544,162 B1 | 4/2003 | Van Wie et al. |
| 2007/0213191 A1 | 9/2007 | Chammas |
| 2010/0048373 A1 | 2/2010 | Rochat |
| 2012/0152957 A1* | 6/2012 | Smith ................. A61L 2/26 220/495.01 |
| 2013/0140226 A1 | 6/2013 | Lundquist et al. |
| 2014/0045672 A1 | 2/2014 | Galavotti et al. |

FOREIGN PATENT DOCUMENTS

| | | |
|---|---|---|
| JP | 04502576 A | 5/1992 |
| JP | H07857 A | 1/1995 |
| JP | 07024451 U | 5/1995 |
| JP | 2004275588 A | 10/2004 |
| JP | 2010042398 A | 2/2010 |
| JP | 2013537071 A | 9/2013 |
| WO | 1985002560 A1 | 6/1985 |
| WO | 1989001827 A1 | 3/1989 |
| WO | 1990007383 A1 | 7/1990 |
| WO | 2012151243 A2 | 11/2012 |

OTHER PUBLICATIONS

International Search Report and Written Opinion issued in PCT/IB2014/065558, dated Aug. 19, 2015, 19 pages.
Invitation to Pay Additional Fees and Partial Search Report issued in PCT/IB2014/065558, dated Jul. 2, 2015, 6 pages.
International Preliminary Report on Patentability issued in PCT/IB2014/065558, dated May 4, 2017, 14 pges.

* cited by examiner

INTEGRATED AUTOTRANSFUSION BOWL AND FLUID LINE ORGANIZER

CROSS-REFERENCE TO RELATED APPLICATION

This application is a national stage application of International Application No. PCT/IB2014/065558, filed Oct. 23, 2014, which is herein incorporated by reference in its entirety.

BACKGROUND

In some medical procedures, in a process known as intraoperative autotransfusion, blood lost by a patient is collected or salvaged to make it available for reinfusion back to the patient. Prior to reinfusion, the collected blood is washed and concentrated to make it safer for the patient. Typically, red blood cells are separated from plasma that contains undesirable elements, such as fat, activated clotting proteins, anticoagulant, activated platelets, coagulation by-products, cellular debris, and free hemoglobin.

In some autotransfusion systems, the components of the blood are separated using a centrifuge bowl. Salvaged blood is put into the centrifuge bowl and the autotransfusion process separates the components of the blood such that the undesirable components can be discarded while retaining and reinfusing the desirable components back to the patient. After use, the centrifuge bowl is discarded.

Existing autotransfusion systems are relatively expensive and fairly complicated. Complicated systems require extensive setup time and can be assembled incorrectly. Moreover, different medical procedures result in greater blood loss, and therefore require centrifuge bowls having different fluid capacities.

SUMMARY

Some aspects relate to an autotransfusion system for separating fluid constituents including a centrifuge housing, the system including a plurality of centrifuge bowls, each of the plurality of bowls having have a different bowl height. A rotatable drive member is mounted within the centrifuge housing and is configured to receive therein and rotationally engage any one of the plurality of centrifuge bowls. The rotatable drive member has a receiving surface and each of the plurality of centrifuge bowls has an exterior configuration sized and shaped to fit within the rotatable drive member, the exterior configuration of each of the plurality of centrifuge bowls is adapted to engage at least a portion of the receiving surface of the rotatable drive member, irrespective of the bowl height, so as to transmit a rotational force from the rotatable drive member to the centrifuge bowl.

Some aspects relate to an autotransfusion system for separating fluid constituents of a fluid including a housing for autotransfusion processing, the autotransfusion system further comprising: a rotatable drive member, the rotatable drive member including a receiving surface configured to receive any one of a plurality of different externally shaped centrifuge bowls; a centrifuge bowl, the centrifuge bowl comprising an exterior configuration adapted to fit within the rotatable drive member, at least a portion of the exterior configuration of the centrifuge bowl adapted to engage a portion of the receiving surface of the rotatable drive member such that the centrifuge bowl can be inserted into and rotationally coupled to the rotatable drive member; and a disposable fluid separation organizer adapted to operatively couple to the centrifuge bowl and removably couple to the housing, the disposable fluid separation organizer including a plurality of fluid lines, the fluid lines configured to facilitate delivery and removal of one or more fluids from the centrifuge bowl.

Some aspects relate to a method of operating an autotransfusion system comprising: removably coupling a housing cover to a centrifuge bowl; inserting the housing cover into a centrifuge housing such that the housing cover and centrifuge housing are in a decoupled state and such that the centrifuge bowl and a rotatable drive member within the centrifuge housing are in a decoupled state; moving the housing cover to an engaged position such that the housing cover is operatively coupled to the centrifuge housing and such that the centrifuge bowl is operatively coupled to the rotatable drive member, wherein moving the housing cover includes moving the housing cover within the centrifuge housing without rotating the housing cover about an axis of rotation of the autotransfusion system.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
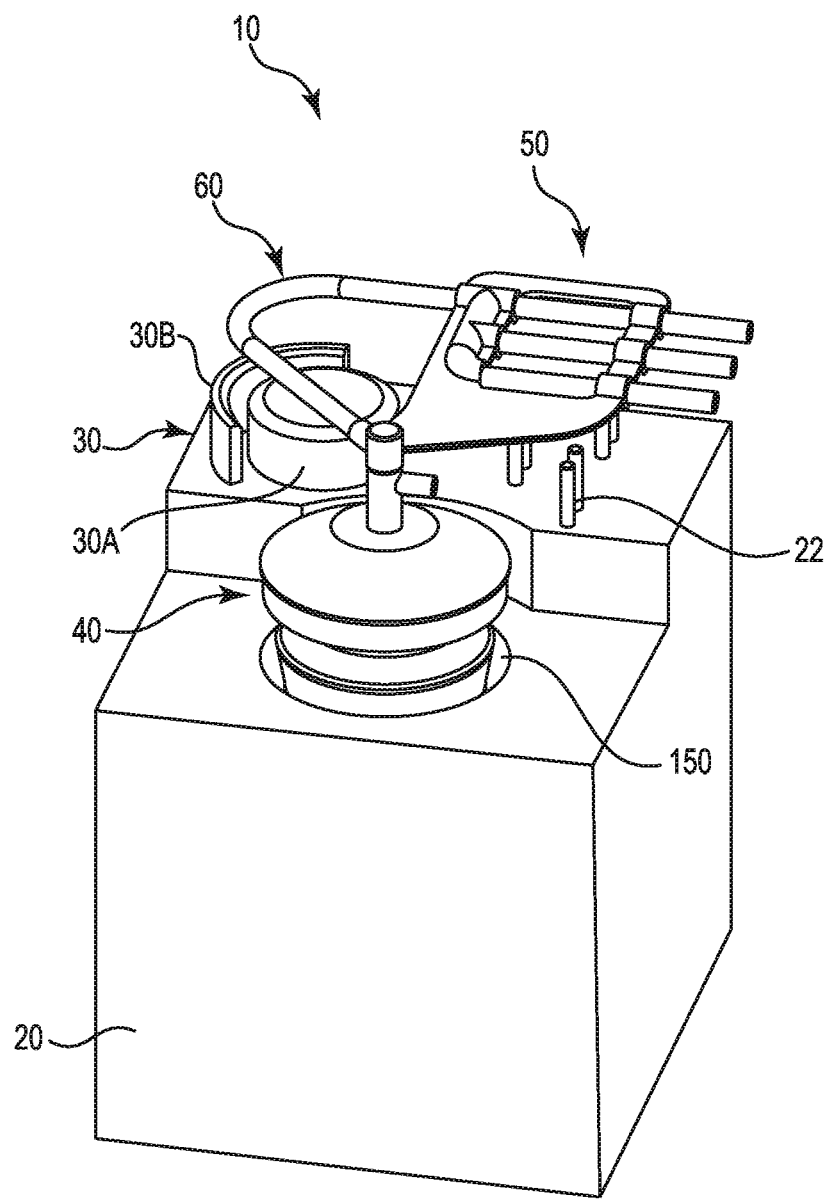
FIG. 1 is a perspective view illustrating an autotransfusion system, according to some embodiments described in the disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 illustrates an autotransfusion system 10, according to some embodiments disclosed herein. The autotransfusion system 10 includes at least a centrifuge housing 20 and a pump 30. In some embodiments, the pump 30 includes a pump drive 30A and a pump line guide 30B. In some embodiments, a centrifuge bowl 40 is situated in the centrifuge housing 20. In some embodiments, the centrifuge bowl 40 is operatively coupled to a fluid line organizer 50 and is additionally or alternatively fluidly coupled to a system fluid line 60. In some embodiments, a controller is operatively coupled to the pump 30 and the centrifuge housing 20, including the centrifuge bowl 40, and is operable to control operation of the autotransfusion system 10. According to various embodiments, the centrifuge bowl 40 (and additionally or alternatively the components of the autotransfusion system 10) are as described in U.S. Pat. No. 5,387,174, the entire contents of which are hereby incorporated by reference.

Figure 2:
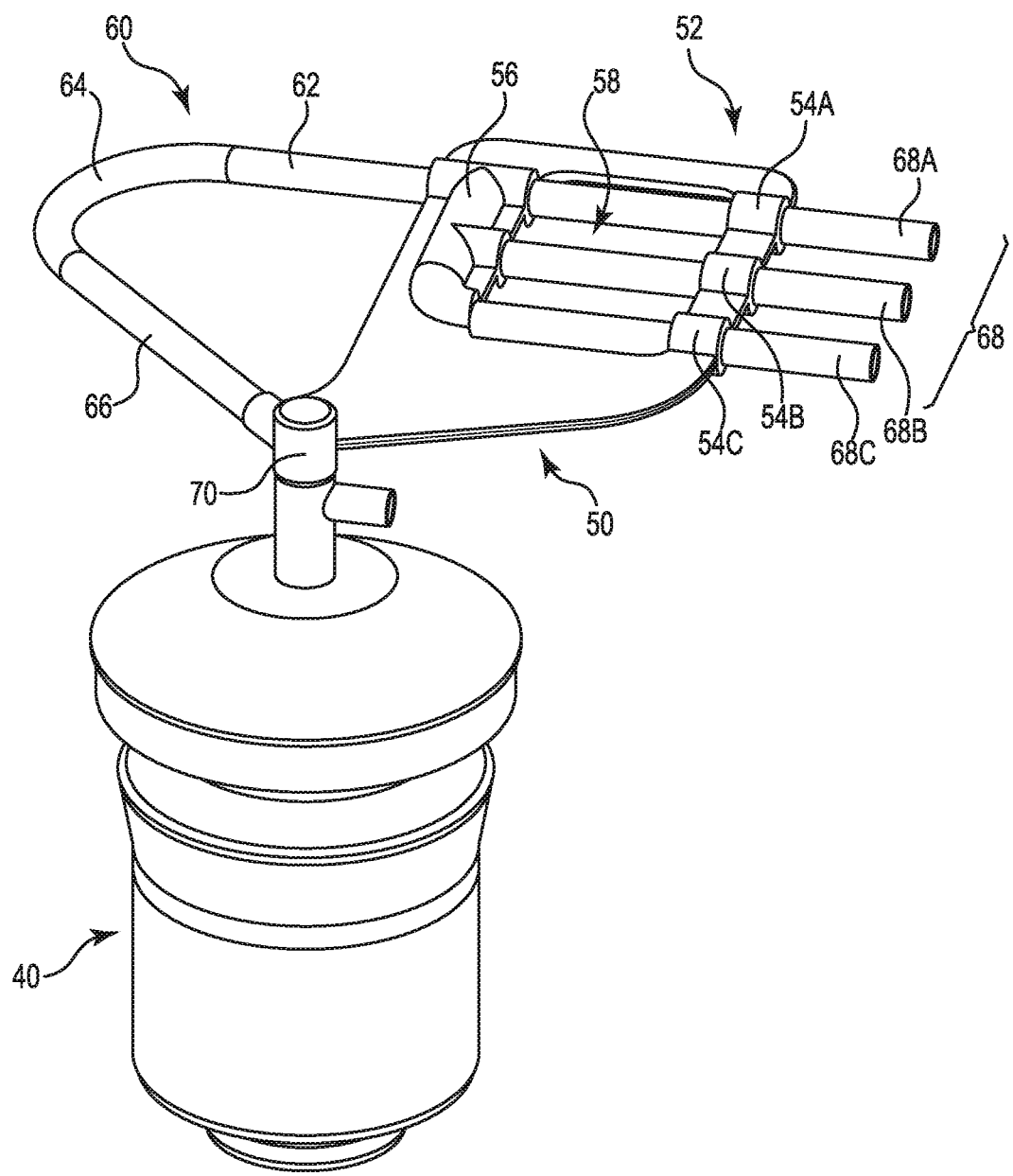
FIG. 2 is a perspective view illustrating an integrated centrifuge bowl and fluid line organizer, according to some embodiments described in the disclosure.

As shown in FIG. 2, in some embodiments, the fluid line organizer 50 is operatively coupled to the centrifuge bowl 40. In some embodiments, the fluid line organizer 50 and the centrifuge bowl 40 are a single, integrated (e.g., one-piece) unit. In these embodiments, the operator of the autotransfusion system 10 may readily and easily insert this integrated unit into the centrifuge housing 20 and, likewise, may readily and easily remove the integrated unit from the centrifuge housing 20. Such an integrated unit may present significant operational efficiencies and advantages for the operator of the autotransfusion system 10.

Optionally, in some other embodiments, the fluid line organizer 50 is removably coupled to the centrifuge bowl 40 such that the autotransfusion system 10 is operable with or without the fluid line organizer 50 coupled to the centrifuge bowl 40. In some such embodiments, the fluid line organizer 50 includes a centrifuge bowl coupler 70 that is configured to receive an inlet tube 106 (FIG. 3) of the centrifuge bowl 40.

In some embodiments, the fluid line organizer 50 includes a frame 52 that is configured to interface with a plurality of fluid lines 68 (such as fluid lines 68A, 68B, and 68C). In some embodiments, the frame 52 provides for proper organization of the plurality of fluid lines 68. In some embodiments, proper organization of fluid lines 68 is facilitated by a plurality of inlets 54 (such as inlets 54A, 54B, and 54C). In some such embodiments, the plurality of inlets 54 are configured to receive there through the plurality of fluid lines 68. Specifically, as is illustrated in FIG. 2, fluid lines 68A, 68B and 68C extend through inlets 54A, 54B, and 54C, respectively.

In some embodiments, the frame 52 further includes a manifold 56 which provides for a transition to a single system fluid line 60. For example, in some embodiments, the plurality of fluid lines 68 entering the manifold 56 transition to a single system fluid line 60. Thus, in some embodiments, the frame 52 facilitates a fluid connection between system fluid line 60 and each fluid line of the plurality of fluid lines 68. In some embodiments, system fluid line 60 and the plurality of fluid lines 68 are integrated into the fluid line organizer 50 during manufacture such that the fluid line organizer 50, system fluid line 60, and the plurality of fluid lines 68 form a single, integrated, disposable unit. In some other embodiments, system fluid line 60 and the plurality of fluid lines 68 are insertable into the fluid line organizer 50 such that they are removably connected to the fluid line organizer 50 and may be inserted and removed.

As further shown in FIG. 2, in some embodiments, a fluid line access section 58 is situated between the plurality of inlets 54 and the manifold 56 of the frame 52. In some embodiments, fluid line access section 58 provides access to (or otherwise exposes) a portion of one or more of the plurality of fluid lines 68 passing through the frame 52. Accordingly, by providing access to one or more of the plurality of fluid lines 68, fluid line access section 58 provides a region for mechanically clamping (via a clamping mechanism 22 such as that shown for example in FIG. 1) of one or more of the fluid lines 68. By clamping one or more of the fluid lines 68, fluid can be prevented from passing through the system line 60 and subsequently entering the centrifuge bowl 40 during an autotransfusion process (such as during the below-discussed filling and/or washing phase of the autotransfusion process). Additionally, or alternatively, by clamping one or more of the fluid lines 68, fluid can be prevented from passing through the one or more fluid lines 68 during the autotransfusion process (such as during the below-discussed emptying phase of the autotransfusion process).

Figure 9A:
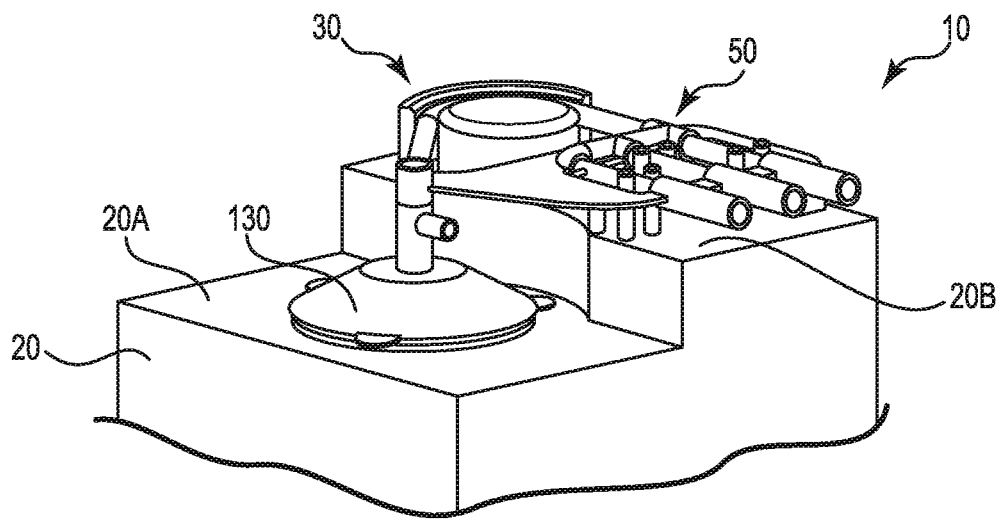
FIGS. 9A and 9B are illustrative views of an autotransfusion system in an engaged, operable state, according to some embodiments described in the disclosure.
Figure 9B:
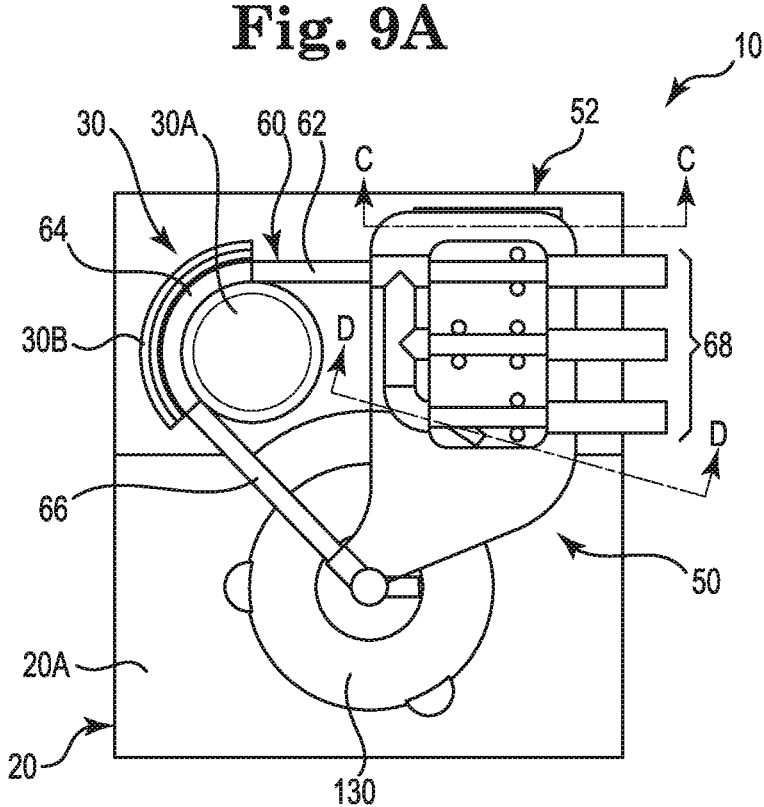

In some embodiments, system fluid line 60 fluidly connects the plurality of fluid lines 68 to an inlet of the centrifuge bowl 40. In some embodiments, the system fluid line 60 includes a manifold line portion 62, a pump line portion 64, and/or a centrifuge bowl inlet portion 66. The manifold line portion 62 fluidly couples to each of the plurality of fluid lines 68. In some embodiments, the frame 52 facilitates such a connection. For example, manifold line portion 62 and fluid lines 68 are fluidly connected at fluid line joining section 56 of the frame 52. The centrifuge bowl inlet portion 66 is fluidly connected with an inlet of the centrifuge bowl 40 such that one or more fluids (such as a patient's blood) being pumped through the system line 60 may enter centrifuge bowl 40 for fluid separation (and may additionally or alternatively exit centrifuge bowl 40 after fluid separation). The pump line portion 64 mechanically interfaces with pump 30 (such as a positive displacement pump or peristaltic pump 30 as shown for example in FIG. 1) of the centrifuge house 20 (FIG. 1). In some embodiments, the pump line portion 64 is generally curved and is situated adjacent to the pump 30 of the autotransfusion system 10 (FIGS. 9A and 9B). In other embodiments, the pump line portion 64 is straight (not curved). Any suitable system or mechanism for pumping fluid through the fluid lines 68 and into (or out of) the centrifuge bowl 40 is envisioned and may be implemented without departing from the scope of the embodiments disclosed herein.

Figure 3:
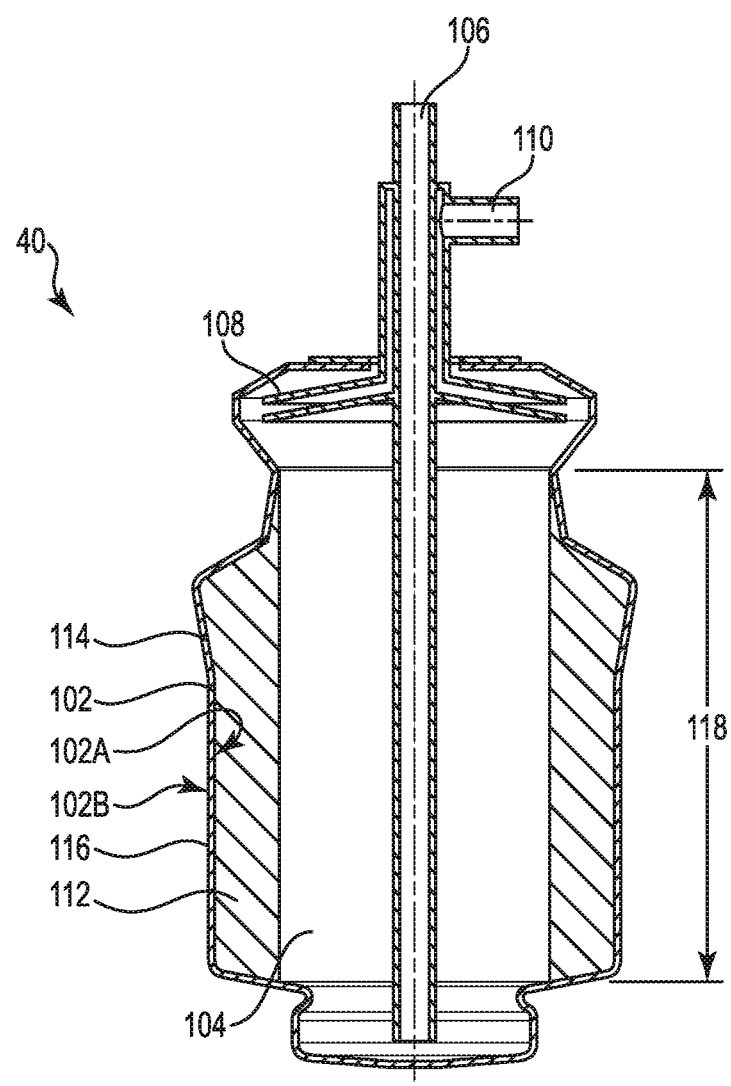
FIG. 3 is a cross-sectional side view illustrating a centrifuge bowl, according to some embodiments described in the disclosure.

As shown in FIG. 3, according to some embodiments, the centrifuge bowl 40 includes an exterior wall 102 (including an interior surface 102A and an exterior surface 102B), a separation chamber 104, an inlet tube 106, a collector 108, and a discharge tube 110. In some embodiments, the exterior wall 102 of the centrifuge bowl 40 includes an upper portion 114 and a lower portion 116. In some embodiments, upper portion 114 is tapered such that a circumference of an exterior surface of the exterior wall 102 of the centrifuge bowl increases as the upper portion 114 extends upward toward a top portion of the centrifuge bowl 40. In some embodiments, the centrifuge bowl 40 is made from an elastomeric material and produced by extrusion blow-molding and has a centrifuge bowl height 118 (such as the below-identified centrifuge bowl heights).

In some embodiments, fluid (such as a patient's blood) enters the separation chamber 104 through an inlet tube 106. The entering fluid travels through inlet tube 106 and exits inlet tube 106 into separation chamber 104 near a bottom portion of the centrifuge bowl 40. As the centrifuge bowl 40 is rotated, the rotation creates a centrifugal force that causes the fluid within the separation chamber 104 to separate into different fractions (or components) based on the density of the components.

For example, centrifugal force created by the rotation of the centrifuge bowl 40 causes the constituent parts of a patient's blood (e.g., red blood cells, white blood cells, platelets, and plasma) to separate according to the relative densities of those constituent parts as would be appreciated by one skilled in the art. Specifically, in the illustrated example of FIG. 3, as the centrifuge bowl rotates, red blood cells 112, which are higher density components of blood, are propelled outward against the interior surface 102A of the exterior wall 102 of the centrifuge bowl 40. Intermediate density blood components (not shown), such as white blood cells and platelets, are similarly propelled outward and, due to their lower density relative to the red blood cells 112, are arranged in a thin layer known as the buffy coat situated directly adjacent the concentrated mass of red blood cells 112. Lower density components (not shown), such as plasma that contains undesirable elements such as fat, are similarly propelled outward and are arranged in a layer situated directly adjacent the buffy coat.

In some embodiments, during fluid separation, the lighter density components travel to a top portion of the centrifuge bowl 40 and are collected and discharged from the separation chamber 104 via the collector 108 and the discharge tube 110. In some embodiments, at a conclusion of the fluid separation process, the fluid remaining in the separation chamber 104 of the centrifuge bowl 40 is pumped (via pump 30 such as shown, for example, in FIG. 1) out of the centrifuge bowl 40 through inlet tube 106. For example, processed blood is pumped out of the centrifuge bowl 40 and into the system line 60 (FIG. 2) by the pump 30 (FIG. 1) and is subsequently stored for reinfusion back to the patient as would be understood by one skilled in the art.

In some embodiments, the autotransfusion system 10 (FIG. 1) is operable with any of a plurality of different sized centrifuge bowls 40. That is, the autotransfusion system 10 is not limited to operate with a single bowl size (i.e., fluid capacity and/or exterior characteristic). For example, the autotransfusion system 10 can include a first centrifuge bowl having a first fluid capacity or a second centrifuge bowl having a second fluid capacity, wherein the second fluid capacity is different from the first fluid capacity. Autotransfusion system 10 is configured to operate with both the first centrifuge bowl and the second centrifuge bowl. Specifically, in some embodiments, a rotatable drive member of the autotransfusion system 10 is configured to operate, individually, with any one of a plurality of differently sized centrifuge bowls.

Figure 4:
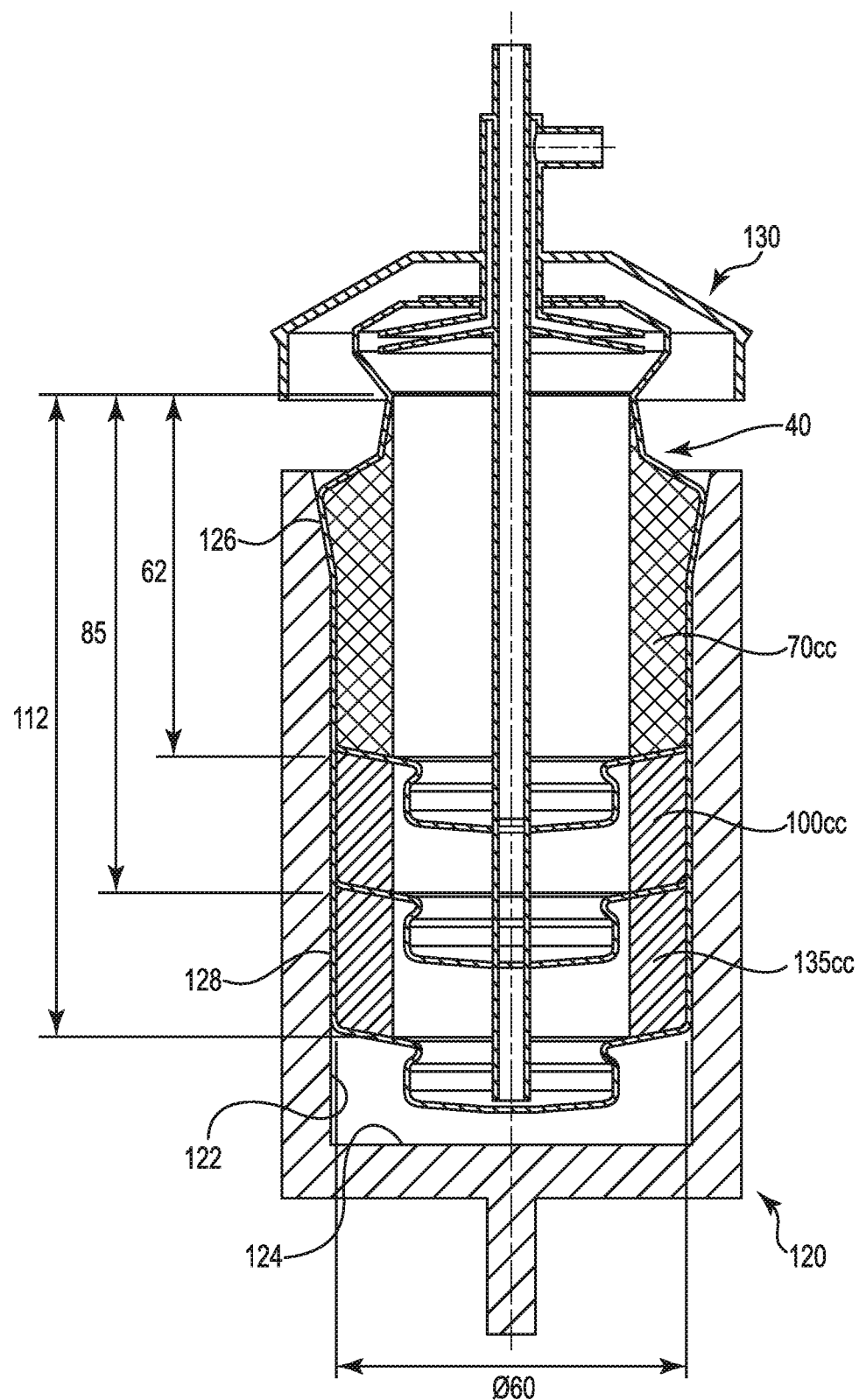
FIG. 4 is a cross-sectional side view illustrating an arrangement of a plurality of different centrifuge bowls in association with a housing cover and a rotatable drive member, according to some embodiments described in the disclosure.

For example, as shown in FIG. 4, the centrifuge housing 20 (FIG. 1) of the autotransfusion system 10 (FIG. 1) includes a rotatable drive member 120. In some embodiments, the rotatable drive member 120 is retained within a housing well 150 of the centrifuge housing 20 (FIG. 1). In some embodiments, the rotatable drive member 120 generally includes an interior surface 122 and a bottom surface 124. In some embodiments, the rotatable drive member 120 includes a tapered upper portion 126 generally forming a conical shape. Tapered upper portion 126 is tapered such that a circumference of a portion of the interior surface 122 increases as the taper extends upward away from the bottom surface 124 of the rotatable drive member 120.

In some embodiments, the centrifuge bowl 40 is operable to be inserted into a rotatable drive member 120. In some embodiments rotatable drive member 120 is cylindrical and is configured to receive the plurality of differently sized centrifuge bowls 40 (discussed below). In some embodiments, centrifuge bowl 40 is frictionally retained within and driven by the rotatable drive member 120. In some embodiments, rotatable drive member 120 is driven by a driving member (not shown), such as a driving motor, situated within the centrifuge housing 20 (FIG. 1). In some such embodiments, the rotatable drive member 120 is removably coupled to the driving member. In some other embodiments, the rotatable drive member 120 is removably coupled to the driving member.

In some embodiments, during an autotransfusion process, the centrifuge bowl 40 is driven in a clockwise direction about a longitudinal axis of the centrifuge bowl 40. In another embodiment, the centrifuge bowl 40 is alternatively driven in a counter-clockwise direction about the longitudinal axis of the centrifuge bowl 40. In yet some other embodiments, the centrifuge bowl 40 is driven in both a clockwise and a counter-clockwise direction about the longitudinal axis of the centrifuge bowl 40. For example, for a first portion of an autotransfusion process, the centrifuge bowl 40 is driven in a first direction about the longitudinal axis of the centrifuge bowl 40 (e.g., clockwise) and for a second portion of the autotransfusion process, the centrifuge bowl 40 is driven in a second, different direction about the longitudinal axis of the centrifuge bowl 40 (e.g., counter-clockwise).

In some embodiments, a top portion of the rotatable drive member 120 is open, exposing the interior surface 122 of the rotatable drive member 120, such that any one of a plurality of different externally sized centrifuge bowls can be received within (or can otherwise be inserted into) the rotatable drive member 120. The illustrated example of FIG. 4 depicts a first centrifuge bowl having a 70 cc fluid capacity, a second centrifuge bowl having a 100 cc fluid capacity and a third centrifuge bowl having a 135 cc fluid capacity. While the plurality of centrifuge bowls illustrated in FIG. 4 are superimposed over one another and appear to be simultaneously received within rotatable drive member 120, the rotatable drive member 120 is configured to individually receive the centrifuge bowls. That is, a single centrifuge bowl 40 is received by the rotatable drive member 120 in association with a given autotransfusion process. For example, the rotatable drive member 120 receives a first centrifuge bowl having a first fluid capacity for a first autotransfusion process and separately and independently receives a second centrifuge bowl having a second (possibly different) fluid capacity for a second autotransfusion process. Similarly, the rotatable drive member 120 receives a third centrifuge bowl having a third fluid capacity for a third autotransfusion process, and so on. Thus, while the rotatable drive member 120 is configured to receive a plurality of differently sized centrifuge bowls, the rotatable drive member 120 is configured to receive such differently sized centrifuge bowls individually.

In some embodiments, the interior surface 122 of the rotatable drive member 120 is configured to accommodate the exterior surface 102B (FIG. 3) of the exterior wall 102 (FIG. 3) of centrifuge bowl 40. In some embodiments, the rotatable drive member 120 receives centrifuge bowl 40 (e.g., centrifuge bowl 40 is inserted into rotatable drive member 120) such that portions of the exterior surface 102B of the centrifuge bowl 40 physically contact portions of the interior surface 122 of the rotatable drive member 120. Specifically, and with reference to the 70 cc capacity centrifuge bowl depicted in FIG. 4, exterior surface 102B of upper tapered portion 114 (FIG. 3) of the exterior wall 102 of the centrifuge bowl 40 physically contacts part of the upper portion 126 of the interior surface 122 of the rotatable drive member 120. Additionally, exterior surface 102B of the lower portion 116 (FIG. 3) of the exterior wall 102 of the centrifuge bowl 40 contacts part of the lower portion 128 of the interior surface 122 of the rotatable drive member 120. In some embodiments, no portion of an inserted centrifuge bowl 40 contacts bottom surface 124 of the rotatable drive member 120. In some other embodiments (not shown), a portion of the inserted centrifuge bowl 40 contacts bottom surface 124 of the rotatable drive member 120.

In some embodiments, the size of a centrifuge bowl 40 is a function of the size (or fluid capacity) of the separation chamber 104 (FIG. 3). In some embodiments, the size (or fluid capacity) of the separation chamber 104 is a function of a diameter Ø60 of an interior surface 102A (FIG. 3) of the exterior wall 102 (FIG. 3) of the centrifuge bowl 40. In some other embodiments, the size (or fluid capacity) of the separation chamber 104 is additionally or alternatively a function of the centrifuge bowl height 118 (e.g., a distance measured between a top and a bottom of a separation chamber of a centrifuge bowl—FIG. 3). For example, a first centrifuge bowl having a first fluid capacity has first height and a second centrifuge bowl having a second, different fluid capacity has a second, different height.

Some measures are reported here below as an example of the separation chamber 40 size being a function of the centrifuge bowl height 118:

| Bowl Size | Small - 70 cc | Medium - 100 cc | Large - 135 cc |
| --- | --- | --- | --- |
| Bowl Height [mm] | 62 | 85 | 112 |
| Bowl Diameter [mm] | 60 | 60 | 60 |

In some embodiments, differing centrifuge bowl heights 118 (FIG. 3) can be accomplished by increasing a length of the lower portion 116 (measured between the bottom of the centrifuge bowl 40 and the upper tapered portion 114 of the centrifuge bowl 40—FIG. 3) of the exterior wall 102 (FIG. 3). For example, referring again to FIG. 4, although the external diameter (and shape) of the lower portion 116 is the same for each of the 70 cc, 100 cc, and 135 cc fluid capacity centrifuge bowls, the length of the lower portion 116 of the exterior wall 102 of the 70 cc fluid capacity centrifuge bowl is different from the length of the lower portion 116 of the exterior walls 102 of each of the 100 cc and 135 cc fluid capacity centrifuge bowls. In this example, the 100 cc and 135 cc fluid capacity centrifuge bowls each have more fluid capacity than the 70 cc fluid capacity centrifuge bowl. While the respective lengths of the lower portions 116 of the 70 cc, 100 cc, and 135 cc fluid capacity centrifuge bowls differ, the 70 cc, 100 cc, and 135 cc fluid capacity centrifuge bowls each properly interface with rotatable drive member 120. In other words, the same rotatable drive member 120 is utilized in association with a plurality of differently sized centrifuge bowls 40.

In some embodiments, the autotransfusion system 10 (FIG. 1) includes a housing cover 130 configured to be coupled to the centrifuge bowl 40. In some embodiments the housing cover 130 is removably coupled to the centrifuge bowl 40 such that the housing cover 130 may be utilized in association with a plurality of different autotransfusion processes and a plurality of different centrifuge bowls 40. In some other embodiments, the housing cover 130 and the centrifuge bowl 40, together, form a single, integrated, disposable unit.

Figure 5:
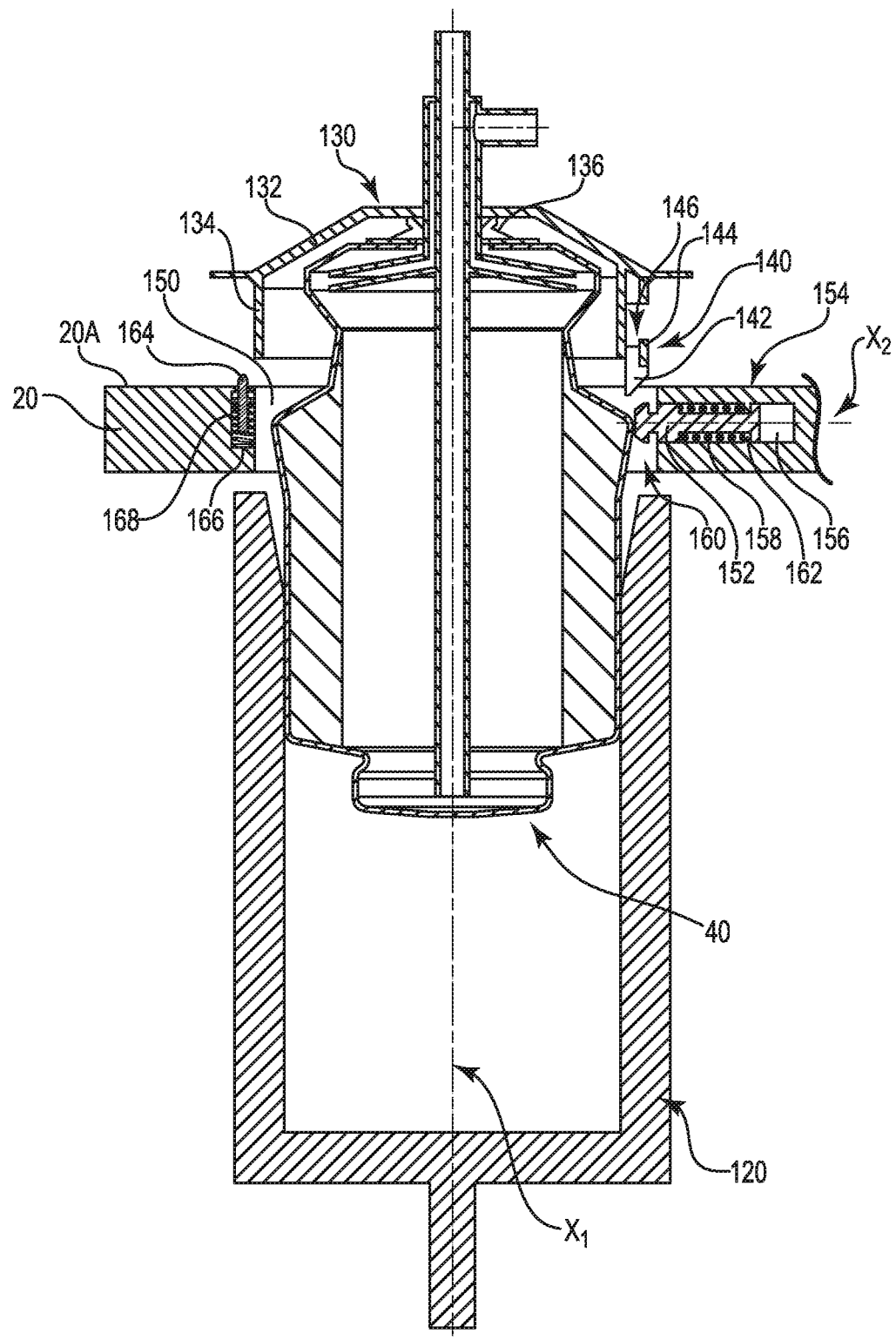
FIG. 5 is a cross-sectional side view illustrating an arrangement of a centrifuge bowl, housing cover, centrifuge housing, and rotatable drive member in a disengaged state, according to some embodiments described in the disclosure.

As shown in FIG. 5, in some embodiments, the housing cover 130 includes a top portion 132 and a side portion 134. In some embodiments, the housing cover 130, the top portion 132, and the side portion 134 are generally cylindrical. In various embodiments, the housing cover 130, the top portion 132, and the side portion 134 could be of any suitable shape provided that housing cover 130 may be properly coupled to the centrifuge bowl 40 (such as a rotating seal) to the centrifuge housing 20 and permit operation of the autotransfusion system 10 (FIG. 1). In some embodiments, the housing cover further includes an interface seal 136 configured to hallow the seal between the centrifuge bowl 40 and the housing cover 130 while permitting the centrifuge bowl 40 to rotate with the rotatable drive member 120 as would be understood by one skilled in the art.

In some embodiments, the housing cover 130 secures the centrifuge bowl 40 to the centrifuge housing 20. For example, as is illustrated in FIG. 5, the housing cover 130 includes a housing engagement feature 140, including a sloped wedge feature 142 and a flange 144. In some embodiments, the sloped wedge feature 142, the flange 144, and the side portion 134, together, create a coupling seat 146. In some embodiments, coupling seat 146 is configured to receive (and thereby retain) an engagement pin 152 of the centrifuge housing 20.

In some embodiments, the centrifuge housing 20 includes a housing well 150. While the housing well 150 shown in the figures is generally cylindrical, the housing well 150 may be of any suitable shape. In some embodiments, an engagement pin 152 is situated in a sidewall of the housing well 150. The engagement pin is retained within an engagement pin housing 154 and includes a proximal end and a distal end, the proximal end being in closer proximity to a longitudinal axis X1 of the housing well 150 than the distal end. In some embodiments, the engagement pin housing 154 permits the engagement pin 152 to translate along a longitudinal axis X2 of the engagement pin housing 154. In some embodiments, the longitudinal axis X2 is perpendicular to the longitudinal axis X1. In some embodiments, the engagement pin housing 154 includes a deflection seat 156 that provides for deflection of the engagement pin 152 (as discussed in greater detail below).

In some embodiments, the engagement pin housing 154 further includes an engagement pin spring 158 (or other elastic component). The engagement pin spring 158 is configured to influence the engagement pin toward the longitudinal axis X1. For example, if the engagement pin 152 is deflected, the engagement pin spring 158 influences the engagement pin 152 to return to its non-deflected state. In some embodiments, the engagement pin housing 154 further includes one or more engagement pin retaining features 162 configured to prevent removal of the engagement pin 152 from the engagement pin housing 154.

In some embodiments, the housing cover 130 is operable to be retained by the engagement pin 152 upon being inserted into housing well 150. For example, the proximal end of the engagement pin 152 includes one or more retaining features configured to properly interface with the housing engagement feature 140 of the housing cover 130. For example, in some embodiments, the proximal end of the engagement pin 152 includes a housing cover retaining feature 160 configured to interface with (or otherwise be retained by) the coupling seat 146 of the housing cover 130. In some embodiments, by retaining the housing cover 130 in the housing well 150, the centrifuge bowl 40 is retained within (and operatively coupled to) the rotatable drive member 120.

FIG. 5 illustrates a position of the centrifuge bowl 40 (including housing cover 130) as it is being inserted into rotatable drive member 120. During insertion, a longitudinal axis of the centrifuge bowl 40 is aligned with the longitudinal axis X1 (which is further aligned with a longitudinal axis of the rotatable drive member 120). Once aligned, and prior to the insertion of the centrifuge bowl 40 into the rotatable drive member 120, engagement pin 152 extends beyond an interior wall of the housing well 150. As the centrifuge bowl 40 is coupled to (e.g., inserted into) the rotatable drive member 120, the housing engagement feature 140 engages the engagement pin 152. In some embodiments, as the engagement feature 140 engages the engagement pin 152 (such as via retaining feature 160), the wedge feature 142 deflects the engagement pin 152 such that the engagement pin 152 translates along the longitudinal axis X2 away from the longitudinal axis X1. In other words, the wedge feature 142 of the housing cover 130 deflects the engagement pin 152 into the deflection seat 156. With the engagement pin 152 deflected into the deflection seat 156, the centrifuge bowl 40 can be fully inserted into (and coupled with) the rotatable drive member 120.

As shown, inserting the centrifuge bowl 40 into the rotatable drive member 120 requires a simple "top-down" translation of the centrifuge bowl 40 and housing cover 130. Specifically, with the centrifuge bowl 40 and housing cover 130 properly aligned with the housing well 150 and rotatable drive member 120, a user need only press down on the top of the housing cover, applying enough downward pressure to cause the centrifuge bowl 40 to be displaced along the longitudinal axis X1 a distance sufficient to cause proper engagement between the rotatable drive member 120 and centrifuge bowl 40 as well as engagement between the engagement feature 140 of the housing cover 130 and the engagement pin 152.

Once the housing cover 130 has been sufficiently displaced along the longitudinal axis X1, engagement pin 152 becomes free to return to its non-deflected position. Accordingly, engagement pin spring 158 influences the engagement pin 152 to translate toward the longitudinal axis X1 such that the housing cover retaining feature 160 properly engages the housing engagement feature 140. Upon proper engagement of housing engagement feature 140 and housing cover retaining feature 160, the housing cover 130 and the centrifuge bowl 40 are operatively coupled to autotransfusion system 10 (FIG. 1) and are prevented from being withdrawn from the housing well 150.

Specifically, once the housing cover 130 has been sufficiently displaced along the longitudinal axis X1 (for example, a distance of approximately 15 mm), flange 144 of the engagement feature 140 is sufficiently displaced such that it no longer obstructs the engagement pin 152 from returning to its non-deflected position. Accordingly, with the engagement pin 152 positioned in its non-deflected position, the proximal end of the engagement pin 152 is situated within the housing well 150 and positioned above the housing engagement feature 140. Accordingly, the housing cover retaining feature 160 engages the coupling seat 146 and thereby retains the housing cover 130 within the housing well 150 and thus causes the centrifuge bowl 40 to be retained within (and operatively coupled to) the rotatable driving member 120.

Figure 6:
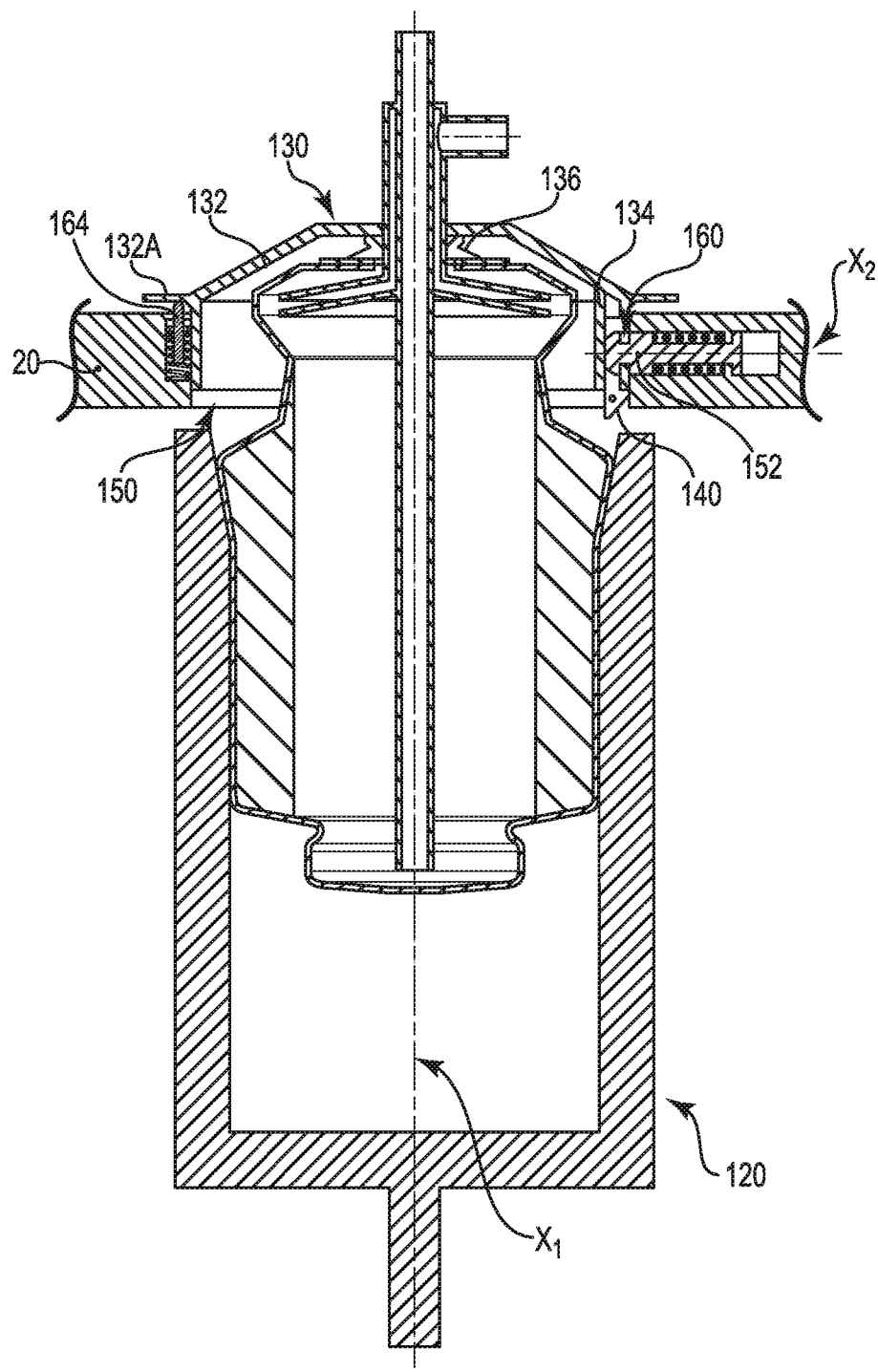
FIG. 6 is a cross-sectional side view illustrating an arrangement of a centrifuge bowl, housing cover, centrifuge housing, and rotatable drive member in an engaged state, according to some embodiments described in the disclosure

FIG. 6 illustrates the coupling between the housing engagement feature 140 and the housing cover retaining feature 160 with the centrifuge bowl 40 fully inserted into the rotatable drive member 120. As illustrated, housing cover retaining feature 160 interfaces with the coupling seat 146 (FIG. 5) to retain the housing cover 130 within the housing well 150. With the housing cover 130 and the centrifuge bowl 40 operatively coupled to autotransfusion system 10 (FIG. 1), the autotransfusion system can initiate an autotransfusion process (such as the above-discussed autotransfusion process).

During the autotransfusion process, the housing cover 130 remains engaged with the engagement pin 152. That is, while centrifuge bowl 40 is free to rotate with the rotatable drive member 120 about the longitudinal axis X1 during the autotransfusion process, the housing cover 130 does not rotate about the axis of rotation X1. Specifically, the centrifuge bowl 40 is free to rotate about the axis of rotation X1 independent of the housing cover 130 by way of interface seal 136.

After a conclusion of the autotransfusion process, the centrifuge bowl 40 and the housing cover 130 are removed from the rotatable drive member 120 and housing well 150 (including rotatable drive member 120). Removal of the centrifuge bowl 40 and the housing cover 130 requires rotating of the housing cover 130 a designated number of degrees (a) about the axis of rotation X1. By rotating the housing cover 130 the designated number of degrees, the housing cover transitions from the above-discussed engaged position or state to a disengaged position or state. In some embodiments, the housing cover 130 is rotated between 20 and 40 degrees (e.g., 30 degrees). However, in various embodiments, any designated degree of rotation may be utilized to disengage the housing cover 130 from the centrifuge housing 20 (such as more than 360 degrees or less than 360 degrees) without departing from the scope of the embodiments disclosed herein.

Figure 7A:
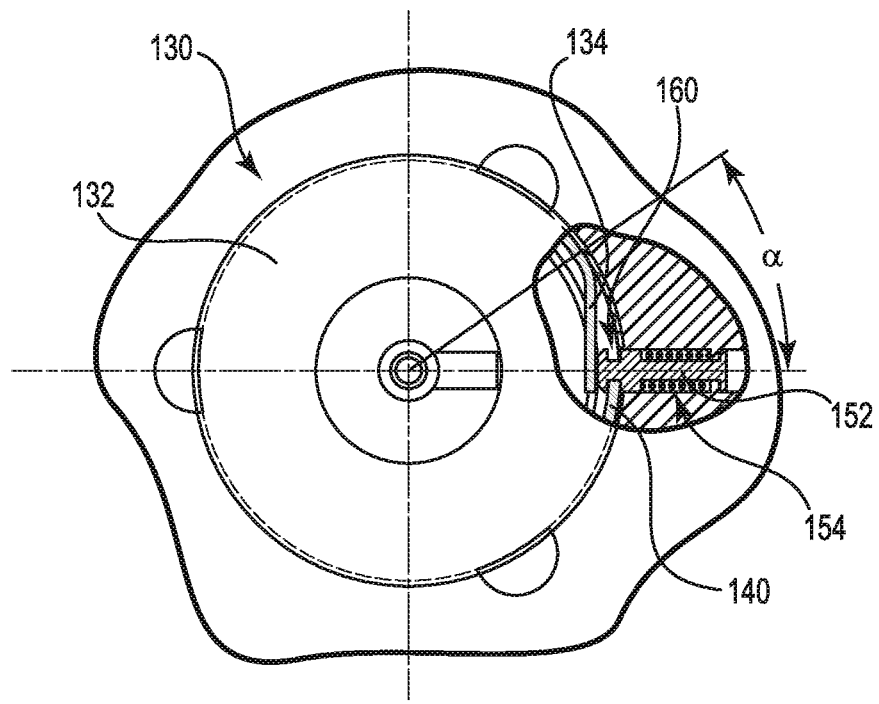
FIG. 7A is a top view including a reveal illustrating the centrifuge bowl, housing cover, centrifuge housing, and rotatable drive member arrangement of FIG. 6.

FIG. 7A illustrates a top view of the above-discussed engaged position with a section of the top portion 132 of the housing cover 130 removed and a section of the centrifuge housing 20 (FIG. 6) removed to reveal the engagement pin 152, the side portion 134, and housing engagement feature 140. During rotation of the housing cover 130 from the engaged position to the disengaged position, the housing engagement feature 140 is decoupled from the housing cover retaining feature 160 and the engagement pin 152 is deflected away from the longitudinal axis X1 toward the deflection seat 156 (FIG. 5).

In some embodiments, a first section of the side portion 134 is a first radial distance from a longitudinal axis of the housing cover 130 and a second section of the side portion 134 is a second, different radial distance from the longitudinal axis of the housing cover 130. Put differently, a continuous side portion 134 of the housing cover 130 includes a plurality of sections varying in radial distance from the longitudinal axis of the housing cover (see FIGS. 7A and 7B). In some such embodiments, as the housing cover 130 is rotated from the engaged position to the disengaged position, side portion 134 contacts the proximal end portion of the engagement pin 152, causing the engagement pin 152 to deflect into the deflection seat 156 (FIG. 5). For example, as the degree of rotation of the housing cover increases, the radial distance of the side portion of the housing cover increases. This increasing radial distance facilitates deflection of the engagement pin 152 into deflection seat 156. With the housing cover 130 rotated the designated number of degrees to the disengaged position, the engagement pin 152 is fully deflected into the deflection seat 156 such that the housing cover 130 can be removed from the housing well 150 (and the centrifuge bowl 40 can be removed or otherwise de-coupled from the rotatable drive member 120—FIG. 5).

Figure 7B:
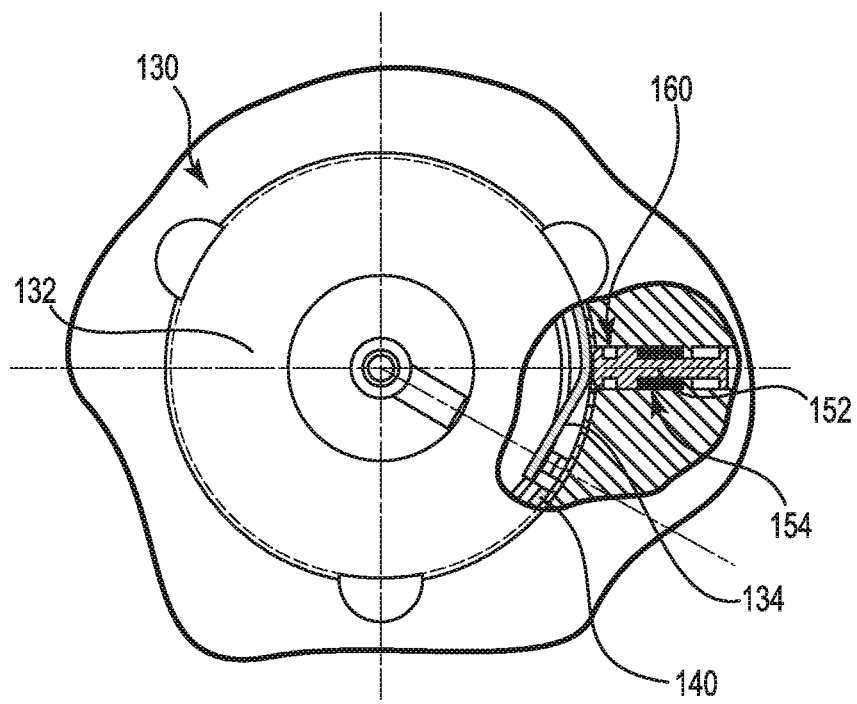
FIG. 7B is a top view including a reveal illustrating the centrifuge bowl, housing cover, centrifuge housing, and rotatable drive member arrangement of FIG. 6 after being rotated to a disengage position, according to some embodiments described in the disclosure.

FIG. 7B illustrates a top view of the above-discussed disengaged position with a section of the top portion 132 of the housing cover 130 removed and a section of the centrifuge housing 20 (FIG. 6) removed to reveal the engagement pin 152, the side portion 134, and the housing engagement feature 140. As illustrated, with the housing cover 130 rotated to the disengaged position, the engagement pin 152 is fully deflected into the deflection seat 156 (FIG. 5) such that the housing engagement feature 140 is decoupled from the housing cover retaining feature 160.

Figure 8:
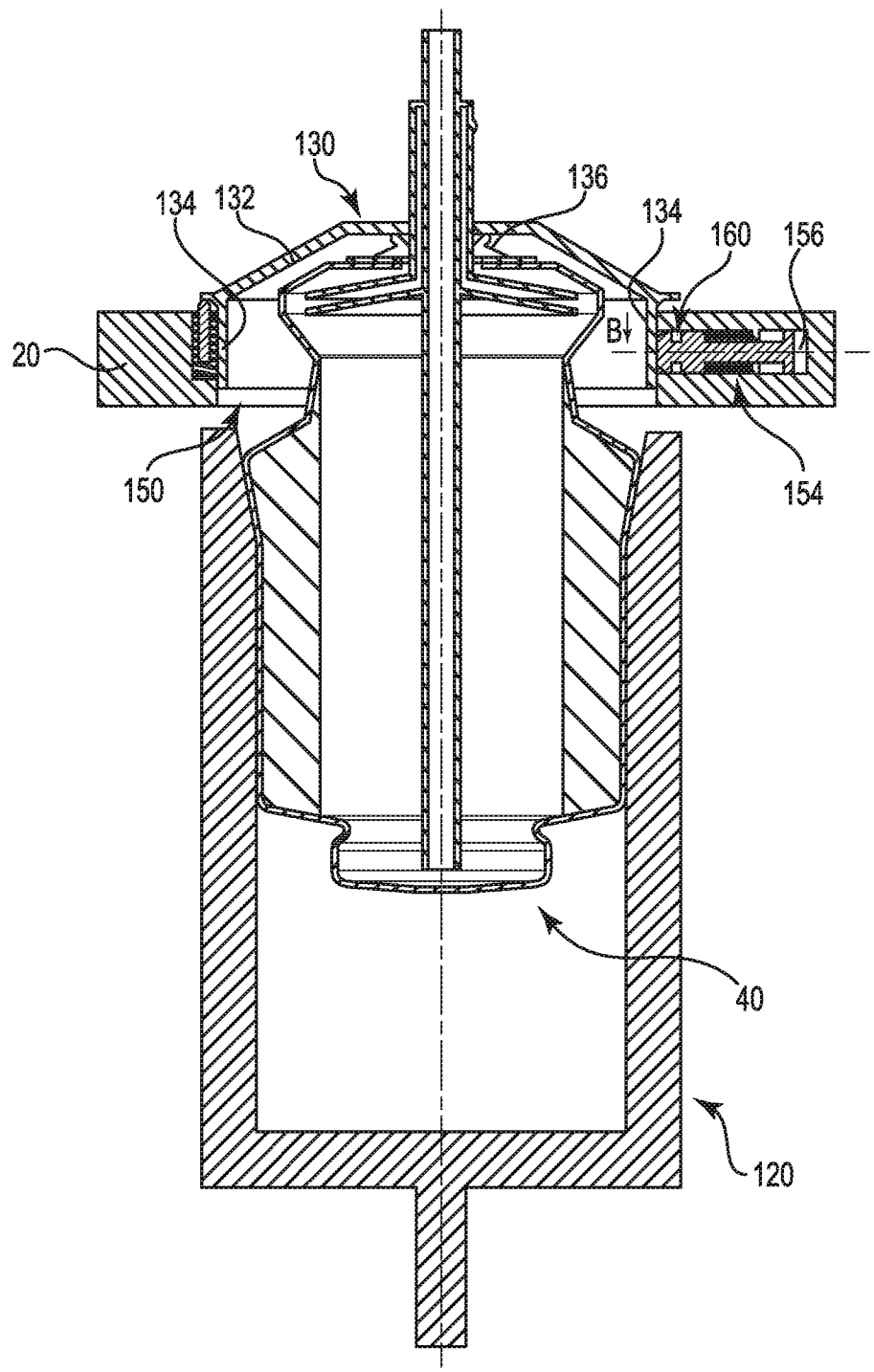
FIG. 8 is a cross-sectional side view of the centrifuge bowl, housing cover, centrifuge housing, and rotatable drive member arrangement illustrated in FIG. 7B.

FIG. 8 provides a cross-sectional side view of the housing cover 130 rotated to the disengaged position and the housing engagement feature 140 (FIG. 7B) decoupled from the housing cover retaining feature 160. Accordingly, the housing cover 130 and the centrifuge bowl 40 can be easily removed from the housing well 150 and the rotatable drive member 120 by lifting the housing cover 130 and the centrifuge bowl 40 out of the housing well 150.

In some embodiments, when rotating the housing cover 130 from the engaged position to the disengaged position, the housing cover 130 is rotated in rotational direction similar to the rotational direction utilized by the rotatable drive member 120 and the centrifuge bowl 40 during the autotransfusion process (e.g., clockwise or counter-clockwise). In some other embodiments, when rotating the housing cover 130 from the engaged position to the disengaged position, the housing cover 130 is rotated in rotational direction different from (or otherwise counter to) the rotational direction utilized by the rotatable drive member 120 and the centrifuge bowl 40 during the autotransfusion process. By requiring the housing cover 130 to be rotated in a direction counter to the direction of rotation of the rotatable drive member 120, the autotransfusion system can avoid accidental decoupling of the housing engagement feature 140 and the housing cover retaining feature 160 during the autotransfusion process.

While the above-discussed examples depict an engaged position between the housing engagement feature 140 and the housing cover retaining feature 160, wherein the housing cover retaining feature 160 of the engagement pin 152 is positioned above the housing engagement feature 140 of the housing cover 130, it should be appreciated that, in some alternative embodiments, the autotransfusion system 10 is additionally or alternatively configured such that the housing cover retaining feature 160 of the engagement pin 152 may be positioned adjacent to (including below and/or to the side of) the housing engagement feature 140 of the housing cover 130 during engagement.

Referring back now to FIG. 5, in some embodiments, the centrifuge housing 20 further includes an alignment pin 164. In some embodiments, the alignment pin 164 resides in an alignment pin seat 166 within the centrifuge housing 20 such that a portion of the alignment pin 164 extends out of the alignment pin seat 166 (and above a top surface 20A of the centrifuge housing 20). In some embodiments, an alignment pin spring 168 is situated within the alignment pin seat 166 and is operable to exert a force upon the alignment pin 164 thereby influencing the alignment pin 164 away from the alignment pin seat 166. In some embodiments, in response to any deflection of the alignment pin 164 into the alignment pin seat 166 (as discussed below), the alignment pin spring 168 influences the alignment pin 164 to return to a non-deflected position.

In some embodiments, upon inserting the housing cover 130 and the centrifuge bowl 40 into the housing well 150, a section of the top portion 132 of the housing cover 130 contacts the alignment pin 164. For example, referring now to FIG. 6, in association with engaging the housing cover 130 with the engagement pin 152, a section 132A of the top portion 132 of the housing cover 130 contacts (and causes deflection of) the alignment pin 164. Alignment pin 164, in turn, exerts a force upon the section 132A of the top portion 132 of the housing cover 130, thereby influencing the housing cover 130 to be properly aligned relative to the centrifuge bowl 40 after centrifuge bowl 40 is fully inserted into (or otherwise operatively coupled to) the rotatable drive member 120 and after the housing cover 130 is properly retained by (or otherwise engaged with) the engagement pin 152. Proper alignment between the centrifuge bowl 40 and the housing cover 130 assures that interface seal 136 functions properly during the autotransfusion process. In other words, with interface seal 136 properly functioning and centrifuge bowl 40 appropriately aligned, centrifuge bowl 40 can effectively and efficiently rotate relative to the housing cover 130 during the autotransfusion process.

FIGS. 9A and 9B illustrate an autotransfusion system 10 in an operating configuration or state, according to some embodiments. As discussed above, in some embodiments, the autotransfusion system includes a fluid line organizer 50 coupled to the centrifuge bowl 40. In some embodiments, the fluid line organizer 50 is operatively coupled to the centrifuge housing 20 in association with insertion of the centrifuge bowl 40 into the rotatable drive member 120 and the housing cover 130 into the housing well 150. In some embodiments, upon coupling the fluid line organizer 50 to the centrifuge housing 20, system fluid line 60 is operatively coupled to the pump 30. For example, as is illustrated in FIG. 9B, pump line portion 64 of the system fluid line 60 is inserted (or otherwise positioned) between pump drive 30A and pump line guide 30B of pump 30. In some embodiments, pump line guide 30B is a generally rigid member configured to operate with the pump drive 30A. During operation of pump 30, pump drive 30A and pump line guide 30B provide for fluid to be drawn through system line 60 (as well as fluid lines 68—FIG. 2). In some embodiments, pump 30 is a peristaltic pump (as discussed above). However, it should be appreciated that the pump 30 depicted in the accompanying figures is for illustrative purposes only, and is not meant to be limiting. Accordingly, it should be appreciated that any suitable system for delivering fluid into centrifuge bowl 40 is envisioned and may be implemented without departing from the scope of the embodiments disclosed herein.

In some embodiments, with the housing cover 130 (and centrifuge bowl 40) retained within the housing well 150, the fluid line organizer 50 is coupled to the centrifuge bowl 40 and is further removably coupled to the centrifuge housing 20 and the pump 30. In some embodiments, fluid line organizer 50 is removably coupled to a top surface 20B of the centrifuge housing 20. In some embodiments, with the housing cover 130 (and centrifuge bowl 40) retained within the housing well 150, pump line portion 64 of the system fluid line 60 is positioned between the pump drive 30A and pump line guide 30B such that fluid can be pumped into and out of the centrifuge bowl 40.

Figure 10:
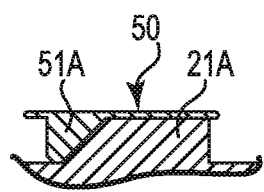
FIGS. 10 and 11 are detail views illustrating interfacing sections of a fluid line organizer and a centrifuge housing, according to some embodiments described in the disclosure.
Figure 11:
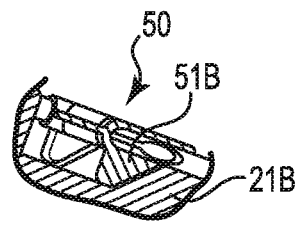

In some embodiments, the centrifuge housing includes one or more fluid line organizer tabs 21 configured to interface with one or more surfaces 51 of the fluid line organizer 50. For example, as is illustrated in FIGS. 10 and 11 (which correspond to detail views C-C and D-D from FIG. 9B, respectively), fluid line organizer tab 21A of centrifuge housing 20 is configured to interface with surface 51A of fluid line organizer 50 (FIG. 10). Similarly, fluid line organizer tab 21B of centrifuge housing 20 is configured to interface with surface 51B of fluid line organizer 50 (FIG. 11). It should be appreciated that, by including one or more interfacing surfaces between the fluid line organizer 50 and the centrifuge housing 20, the autotransfusion system provides for proper support and alignment of the fluid line organizer 50 relative to the centrifuge housing 20. In some embodiments, the one or more fluid line organizer tabs 21 and the one or more surfaces 51 include sloped surfaces (FIGS. 10 and 11). In some embodiments, by including sloped surfaces on the one or more fluid organizer tabs 21 and/or the one or more surfaces 51, the autotransfusion system 10 provides for easy removal of the fluid line organizer 50 from the centrifuge housing 20.

In some embodiments, after completion of the autotransfusion process, the fluid line organizer 50, including the system fluid line 60 and fluid lines 68, is removed from the centrifuge housing 20. In some embodiments, as disclosed herein, the housing cover 130 is rotated and disengaged from the centrifuge housing 20 during removal. In some embodiments, prior to rotation of the housing cover 130, the system fluid line 60 is disconnected from the pump 30. In some embodiments, system fluid line 60 is disconnected from the pump 30 by removing the pump line portion 64 from its operating position between the pump drive 30A and pump line guide 30B. In some embodiments, after removal of the system fluid line 60 from the pump 30, the housing cover 130 is free to be rotated from the engaged position to the disengaged position. It should be appreciated, however, that in some embodiments, the housing cover 130 may be rotated from the engaged position to the disengaged position prior to removal of the system fluid line 60 from the pump 30. For example, as discussed above, in some embodiments, the fluid line organizer is free to rotate relative to the housing cover 130 (or is alternatively detachable) from the centrifuge bowl 40. Accordingly, decoupling the system fluid line 60 from the pump 30 can be performed independent from (and therefore before, during, or after) decoupling the housing cover 130 from the centrifuge housing 20.

Figure 12A:
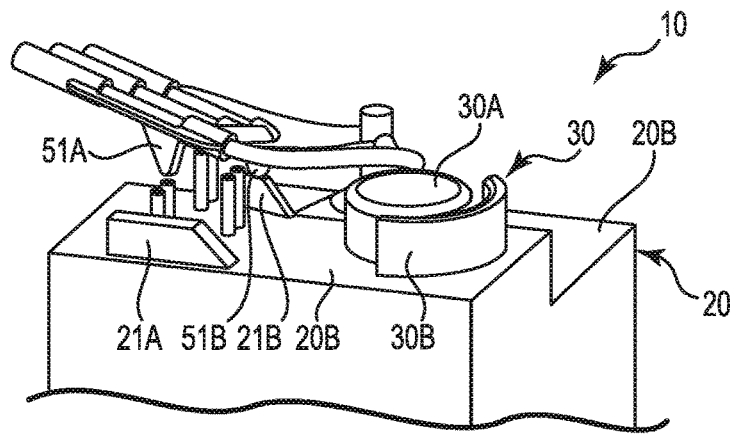
FIGS. 12A to 12C are illustrative views of an autotransfusion system in a disengaged, inoperable state, according to some embodiments described in the disclosure.
Figure 12B:
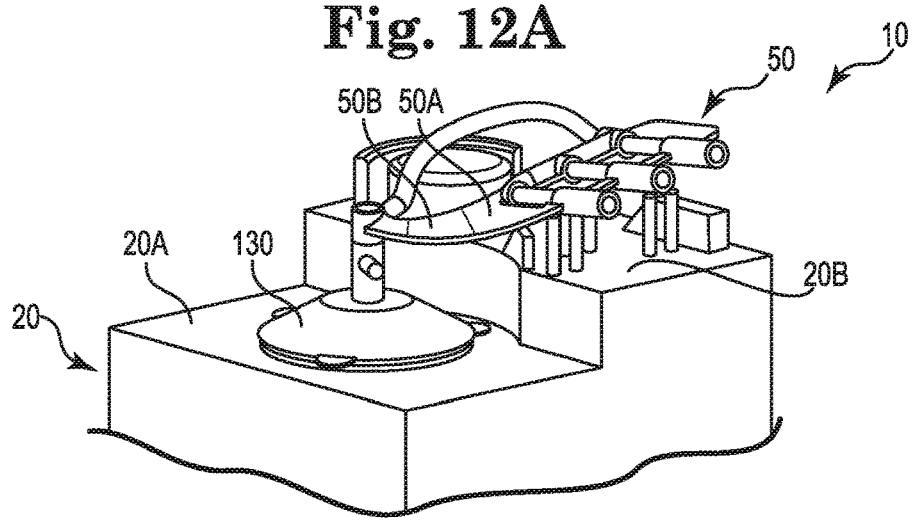
Figure 12C:
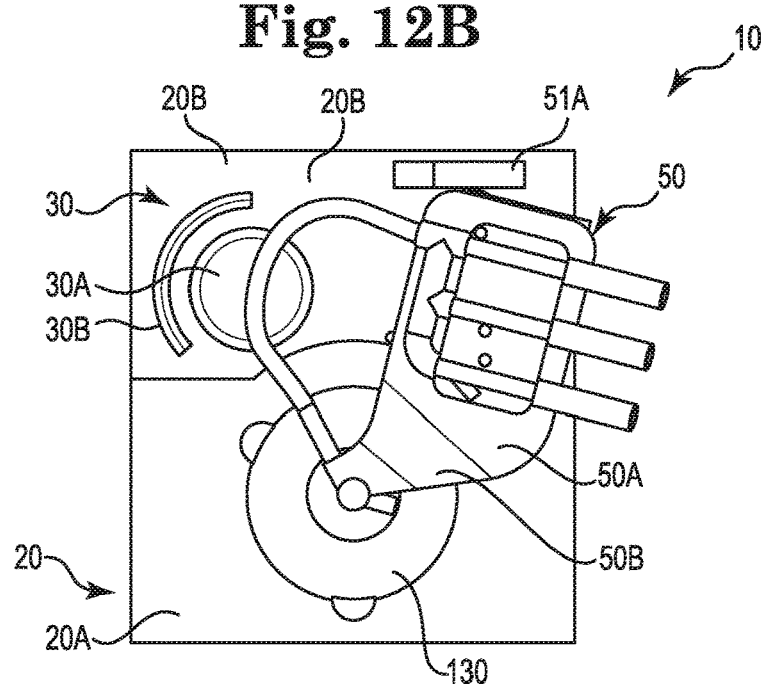

FIGS. 12A to 12C illustrate an autotransfusion system 10 in a non-operating configuration or state, according to some embodiments. In some embodiments, as the housing cover 130 is rotated from the engaged position or state to the disengaged position or state, the fluid line organizer 50 is similarly rotated. That is, in some embodiments, the fluid line organizer 50 rotates in lock-step (or substantially in lock-step) with the rotation of the housing cover 130. In some other embodiments, the fluid line organizer 50 is free to rotate independent (or substantially independent) of the housing cover 130. Accordingly, in these embodiments, the fluid line organizer 50 may be removed prior to (or alternatively during, or after) disengaging the housing cover 130 from the centrifuge housing 20.

In some embodiments, the fluid line organizer is comprised of a plurality of different sections (e.g., 50A and 50B). In some embodiments, each of the plurality of the sections are rigid, non-deflectable sections (e.g., formed of a rigid elastomeric material). In some other embodiments, one or more of the plurality of sections maintain a designated degree of flexibility such that they are operable to permit one or more portions (such as the manifold portion 52—FIG. 2) of the fluid line organizer 50 to deflect (or otherwise change orientation) relative to the centrifuge housing 20. In some such embodiments, upon rotating the housing cover 130 from the engaged position to the disengaged position, the fluid line organizer 50 is additionally deflected away from the top surface 20B of the centrifuge housing 20. As is illustrated in FIGS. 12A to 12C, the fluid line organizer 50 is configured to bend at a deflection portion 50B, such that portion 50A of the fluid line organizer may be deflected away from the top surface 20B of the centrifuge housing 20.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An autotransfusion system for separating fluid constituents including a centrifuge housing, the system comprising:
    a plurality of centrifuge bowls, each of the plurality of bowls having a different bowl height;
    a rotatable drive member mounted within the centrifuge housing, the rotatable drive member configured to receive therein and rotationally engage any one of the plurality of centrifuge bowls,
    wherein the rotatable drive member has a receiving surface and each of the plurality of centrifuge bowls has an exterior configuration sized and shaped to fit within the rotatable drive member, the exterior configuration of each of the plurality of centrifuge bowls is adapted to engage at least a portion of the receiving surface of the rotatable drive member, irrespective of the bowl height, so as to transmit a rotational force from the rotatable drive member to the centrifuge bowl; and
    a housing cover configured to be removably coupled to any one of the plurality of centrifuge bowls and configured to be moved within the centrifuge housing without rotating the housing cover about a longitudinal axis of rotation of the rotatable drive member to operatively couple the housing cover to the centrifuge housing and to operatively couple any one of the plurality of centrifuge bowls to the rotatable drive member.

2. The autotransfusion system of claim 1, wherein the housing cover is configured to be operatively coupled to the centrifuge housing so as to retain the centrifuge bowl within the rotatable drive member.

3. The autotransfusion system of claim 2, wherein the centrifuge housing includes a housing cover engagement feature and the housing cover includes a centrifuge housing engagement feature, the housing cover engagement feature of the centrifuge housing being operable to interface with the centrifuge housing engagement feature of the housing cover to cause the housing cover to be retained in an engaged position within the centrifuge housing.

4. The autotransfusion system of claim 3, wherein the housing cover engagement feature of the centrifuge housing includes a deflectable pin situated within a deflection seat, and wherein the centrifuge housing engagement feature of the housing cover includes at least a deflection feature and a retaining seat feature, the deflection feature being configured to deflect the deflectable pin into the deflection seat, and the retaining seat feature being configured to interface with the deflection pin such that the housing cover is retained by the deflection pin within the centrifuge housing.

5. The autotransfusion system of claim 4, wherein the deflection pin is deflectable along a longitudinal axis of the deflection pin, the longitudinal axis of the deflection pin being perpendicular to the longitudinal axis of rotation of the rotatable drive member.

6. The autotransfusion system of claim 1, further comprising a fluid line organizer, the fluid line organizer being operatively coupleable to any of the plurality of centrifuge bowls and being removably coupleable to the centrifuge housing, the fluid line organizer including a plurality of fluid lines configured to facilitate delivery and removal of one or more fluids from any of the plurality of centrifuge bowls coupled to the fluid line organizer.

7. The autotransfusion system of claim 6, wherein the fluid line organizer is coupled to one of the plurality of centrifuge bowls such that the fluid line organizer and the coupled centrifuge bowl, together, form a single, integrated unit.

8. The autotransfusion system of claim 1, wherein the plurality of centrifuge bowls have different fluid capacities.

9. The autotransfusion system of claim 1, wherein at least one of the plurality of centrifuge bowls engages a larger portion of the receiving surface of the rotatable drive member relative to the other centrifuge bowls of the plurality of centrifuge bowls.

10. The autotransfusion system of claim 1, wherein the autotransfusion system is operable for a plurality of independent fluid separation processes and includes:
a single independent centrifuge bowl selected from the plurality of centrifuge bowls for an independent fluid constituent separation process, the single independent centrifuge bowl being operatively coupled to the rotatable drive member for the single independent fluid constituent separation process.

11. An autotransfusion system for separating fluid constituents including a centrifuge housing, the system comprising:
a plurality of centrifuge bowls, each of the plurality of bowls having a different bowl height;
a rotatable drive member mounted within the centrifuge housing, the rotatable drive member configured to receive therein and rotationally engage any one of the plurality of centrifuge bowls,
wherein the rotatable drive member has a receiving surface and each of the plurality of centrifuge bowls has an exterior configuration sized and shaped to fit within the rotatable drive member, the exterior configuration of each of the plurality of centrifuge bowls is adapted to engage at least a portion of the receiving surface of the rotatable drive member, irrespective of the bowl height, so as to transmit a rotational force from the rotatable drive member to the centrifuge bowl, and
wherein the plurality of centrifuge bowls have different fluid capacities and at least one of the plurality of centrifuge bowls engages a larger portion of the receiving surface of the rotatable drive member relative to the other centrifuge bowls of the plurality of centrifuge bowls.

12. The autotransfusion system of claim 11, comprising a housing cover configured to be removably coupled to any one of the plurality of centrifuge bowls and configured to be moved within the centrifuge housing without rotating the housing cover about a longitudinal axis of rotation of the rotatable drive member to operatively couple the housing cover to the centrifuge housing and to operatively couple any one of the plurality of centrifuge bowls to the rotatable drive member.

13. The autotransfusion system of claim 11, comprising a housing cover configured to be removably coupled to any one of the plurality of centrifuge bowls, the housing cover configured to be operatively coupled to the centrifuge housing to retain the centrifuge bowl within the rotatable drive member.

14. The autotransfusion system of claim 13, wherein the centrifuge housing includes a housing cover engagement feature and the housing cover includes a centrifuge housing engagement feature, the housing cover engagement feature of the centrifuge housing being operable to interface with the centrifuge housing engagement feature of the housing cover to cause the housing cover to be retained in an engaged position within the centrifuge housing.

15. The autotransfusion system of claim 11, comprising a fluid line organizer, the fluid line organizer being operatively coupleable to any of the plurality of centrifuge bowls and being removably coupleable to the centrifuge housing, the fluid line organizer including a plurality of fluid lines configured to facilitate delivery and removal of one or more fluids from any of the plurality of centrifuge bowls coupled to the fluid line organizer.

16. An autotransfusion system for separating fluid constituents including a centrifuge housing, the system comprising:
a plurality of centrifuge bowls, each of the plurality of bowls having a different bowl height;
a rotatable drive member mounted within the centrifuge housing, the rotatable drive member configured to receive therein and rotationally engage any one of the plurality of centrifuge bowls,
wherein the rotatable drive member has a receiving surface and each of the plurality of centrifuge bowls has an exterior configuration sized and shaped to fit within the rotatable drive member, the exterior configuration of each of the plurality of centrifuge bowls is adapted to engage at least a portion of the receiving surface of the rotatable drive member, irrespective of the bowl height, so as to transmit a rotational force from the rotatable drive member to the centrifuge bowl; and
a fluid line organizer, the fluid line organizer being operatively coupleable to any of the plurality of centrifuge bowls and being removably coupleable to the centrifuge housing, the fluid line organizer including a plurality of fluid lines configured to facilitate delivery and removal of one or more fluids from any of the plurality of centrifuge bowls coupled to the fluid line organizer.

17. The autotransfusion system of claim 16, wherein the fluid line organizer is coupled to one of the plurality of centrifuge bowls such that the fluid line organizer and the coupled centrifuge bowl, together, form a single, integrated unit.

18. The autotransfusion system of claim 16, wherein the plurality of centrifuge bowls have different fluid capacities.

19. The autotransfusion system of claim 16, wherein at least one of the plurality of centrifuge bowls engages a larger portion of the receiving surface of the rotatable drive member relative to the other centrifuge bowls of the plurality of centrifuge bowls.

20. The autotransfusion system of claim 16, comprising a housing cover configured to be removably coupled to any one of the plurality of centrifuge bowls and configured to be moved within the centrifuge housing without rotating the housing cover about a longitudinal axis of rotation of the rotatable drive member to operatively couple the housing cover to the centrifuge housing and to operatively couple any one of the plurality of centrifuge bowls to the rotatable drive member.

* * * * *